US009101537B2

(12) United States Patent
Van Wyk et al.

(10) Patent No.: US 9,101,537 B2
(45) Date of Patent: Aug. 11, 2015

(54) COMPOSITIONS AND METHODS FOR THE PREVENTION AND TREATMENT OF CARDIOVASCULAR DISEASES

(75) Inventors: Henk Van Wyk, Denver, CO (US); Mariette Van Wyk, Denver, CO (US); Trace Krebs, Sarasota, FL (US); Peter Lange, Denver, CO (US); Brian Denomme, Northville, MI (US); Michael A. Volk, Broomfield, CO (US)

(73) Assignee: REVEN PHARMACEUTICALS, INC., Golden, CO (US)

( * ) Notice: Subject to any disclaimer, the term of this patent is extended or adjusted under 35 U.S.C. 154(b) by 651 days.

(21) Appl. No.: 13/055,691

(22) PCT Filed: Jul. 24, 2009

(86) PCT No.: PCT/US2009/051694
§ 371 (c)(1),
(2), (4) Date: Apr. 14, 2011

(87) PCT Pub. No.: WO2010/011927
PCT Pub. Date: Jan. 28, 2010

(65) Prior Publication Data
US 2011/0262563 A1 Oct. 27, 2011

Related U.S. Application Data

(60) Provisional application No. 61/129,883, filed on Jul. 25, 2008.

(51) Int. Cl.
| | | |
|---|---|---|
| *A01N 59/08* | (2006.01) |
| *A61K 33/14* | (2006.01) |
| *A61K 9/00* | (2006.01) |
| *A61K 31/375* | (2006.01) |
| *A61K 31/4415* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 33/00* | (2006.01) |
| *A61K 33/06* | (2006.01) |

(52) U.S. Cl.
CPC ............ *A61K 9/0019* (2013.01); *A61K 31/375* (2013.01); *A61K 31/4415* (2013.01); *A61K 31/455* (2013.01); *A61K 31/51* (2013.01); *A61K 31/519* (2013.01); *A61K 31/525* (2013.01); *A61K 33/00* (2013.01); *A61K 33/06* (2013.01); *A61K 33/14* (2013.01)

(58) Field of Classification Search
USPC ........................................................ 424/681
See application file for complete search history.

(56) References Cited

U.S. PATENT DOCUMENTS

| | | | |
|---|---|---|---|
| 5,607,934 A | 3/1997 | Tone et al. |
| 5,736,027 A | 4/1998 | Nakamura |
| 5,938,915 A | 8/1999 | Morisawa |
| 6,251,259 B1 | 6/2001 | Satoh |
| 6,344,181 B2 | 2/2002 | Boykin |
| 6,426,066 B1 | 7/2002 | Najafi |
| 6,506,392 B2 * | 1/2003 | Siamon ..................... 424/401 |
| 6,544,401 B1 | 4/2003 | Colic |
| 6,544,502 B2 | 4/2003 | Heesch |
| 6,649,193 B1 | 11/2003 | Colic |
| 6,942,767 B1 | 9/2005 | Fazzina |
| 6,968,382 B2 | 11/2005 | McBrearty et al. |
| 7,018,623 B2 | 3/2006 | Barclay |
| 7,374,645 B2 | 5/2008 | Davis et al. |
| 7,588,488 B2 | 9/2009 | Hopkins et al. |
| 7,691,249 B2 | 4/2010 | Daly et al. |
| 8,367,120 B1 | 2/2013 | Norton et al. |
| 8,455,010 B1 | 6/2013 | Norton et al. |
| 2001/0022273 A1 | 9/2001 | Popov et al. |
| 2001/0048915 A1 | 12/2001 | Boykin |
| 2002/0014460 A1 | 2/2002 | McKay |
| 2002/0023847 A1 | 2/2002 | Natsume |
| 2002/0027079 A1 | 3/2002 | Hanaoka |
| 2002/0035087 A1 | 3/2002 | Barclay |
| 2002/0158018 A1 | 10/2002 | Abramowitz et al. |
| 2002/0160053 A1 | 10/2002 | Yahagi et al. |
| 2002/0165220 A1 | 11/2002 | Heesch |
| 2002/0176885 A1 | 11/2002 | Najafi et al. |
| 2002/0179455 A1 | 12/2002 | Hanaoka |
| 2002/0185380 A1 | 12/2002 | Hanaoka |
| 2003/0014522 A1 | 1/2003 | McBrearty et al. |
| 2003/0049163 A1 | 3/2003 | Malchesky |
| 2003/0089618 A1 | 5/2003 | Satoh |
| 2003/0175220 A1 | 9/2003 | Wang et al. |
| 2004/0013768 A1 | 1/2004 | Khatchatrian |
| 2004/0037896 A1 | 2/2004 | Ernst |
| 2004/0094406 A1 | 5/2004 | Sawada |

(Continued)

FOREIGN PATENT DOCUMENTS

| | | |
|---|---|---|
| EP | 1238945 A1 | 9/2002 |
| EP | 1550637 A1 | 7/2005 |

(Continued)

OTHER PUBLICATIONS

Hsu (Journal of Food Engineering 66 (2005) 171-176).*

(Continued)

*Primary Examiner* — David J Blanchard
*Assistant Examiner* — Devang Thakor

(57) ABSTRACT

Compositions comprising electro-activated aqueous solutions and methods for the prevention and treatment of dysfunctional cardiovascular conditions are provided.

2 Claims, No Drawings

(56) References Cited

U.S. PATENT DOCUMENTS

| | | |
|---|---|---|
| 2004/0131695 A1 | 7/2004 | Hinze |
| 2004/0137078 A1* | 7/2004 | Najafi et al. .................. 424/661 |
| 2005/0006592 A1 | 1/2005 | Kitada |
| 2005/0029198 A1 | 2/2005 | Tepper et al. |
| 2005/0139808 A1* | 6/2005 | Alimi ...................... 252/187.26 |
| 2005/0175759 A1 | 8/2005 | Singhal |
| 2006/0008908 A1 | 1/2006 | Giles |
| 2006/0065544 A1 | 3/2006 | Hanaoka |
| 2006/0191785 A1 | 8/2006 | Ito et al. |
| 2006/0235350 A1 | 10/2006 | Alimi et al. |
| 2006/0263441 A1 | 11/2006 | Fukui et al. |
| 2006/0275498 A1 | 12/2006 | Bagley |
| 2007/0023273 A1 | 2/2007 | Kitaori et al. |
| 2007/0148256 A1 | 6/2007 | Yanagihara et al. |
| 2007/0166547 A1 | 7/2007 | Dobbertin et al. |
| 2007/0261950 A1 | 11/2007 | Sato |
| 2008/0047844 A1 | 2/2008 | Miyashita |
| 2009/0214628 A1 | 8/2009 | de Rijk |
| 2013/0236563 A1 | 9/2013 | Samuelson et al. |
| 2013/0243883 A1 | 9/2013 | Norton et al. |
| 2014/0044800 A1 | 2/2014 | Robinson et al. |
| 2014/0050800 A1 | 2/2014 | Nieman et al. |
| 2014/0056991 A1 | 2/2014 | Nieman et al. |

FOREIGN PATENT DOCUMENTS

| | | | |
|---|---|---|---|
| EP | 1721868 | A1 | 11/2006 |
| EP | 1748080 | | 1/2007 |
| JP | 10272468 | A | 10/1998 |
| JP | 2000033377 | A | 2/2000 |
| JP | 2003340453 | A | 12/2003 |
| JP | 2006098003 | A | 4/2006 |
| JP | 2006-255613 | * | 9/2006 |
| WO | 00/71476 | | 11/2000 |
| WO | 01/19365 | A1 | 3/2001 |
| WO | WO 01/19365 | * | 3/2001 |
| WO | 01/54704 | A1 | 8/2001 |
| WO | 02/069955 | A1 | 9/2002 |
| WO | 03/037802 | A1 | 5/2003 |
| WO | 03/050044 | A1 | 6/2003 |
| WO | 2006/025563 | A1 | 3/2006 |
| WO | 2006/035523 | A1 | 4/2006 |
| WO | 2006/098405 | A1 | 9/2006 |
| WO | 2006/107760 | | 10/2006 |
| WO | 2007/072147 | A2 | 6/2007 |
| WO | 2007/140544 | A1 | 12/2007 |
| WO | 2008/041031 | A1 | 4/2008 |
| WO | 2009/083989 | | 7/2009 |

OTHER PUBLICATIONS

Bisla (Investigative Ophthalmology & Visual Science, vol. 33, No. 11, Oct. 1992).*
USPTO STIC structure search for Claim 2 of 13/055691.*
CDC (http://www.cdc.gov/niosh/idlh/100378.HTML; May 1994; accessed Nov. 25, 2013).*
Lenfant (Biomedicine & Pharmacotherapy 58 (2004) 248-254).*
Auerbach (The Lancet, vol. 369, Issue 9572, May 5-11, 2007, pp. 1502-1504).*
Shiga (JP2006-255613, Sep. 28, 2006; machine translation).*
Kishi (The American Journal of Clinical Nutrition 32: February 1979, pp. 332-338).*
Medline (http://www.nlm.nih.gov/medlineplus/druginfo/natural/853.html; accessed Apr. 5, 2015).*
Petitclerc (Nephrol Dial Transplant (1999) 14:2607-2613).*
Desai et al. (2004) Cosmetic Dermatology:17(2) 93-105.
14/481,595.
61/001,101.
International Search Report for PCT/US2009/051694.
International Preliminary Report on Patentability for PCT/US2009/051694.
Bisla et al., "Concentration-Dependent Effects of Lidocaine on Corneal Epithelial Wound Healing," Investigative Ophthalmology and Visual Science, vol. 33, No. 11, pp. 3029- 3033 (Oct. 1992).
Hsu, "Effects of flow rate, temperature and salt concentration on chemical and physical properties of electrolyzed oxidizing water," Journal of Food Engineering 66, pp. 171-176 (2005).
USPTO STIC Structure Search for Claim 2 of 14/550,677 (2015).
Martinez-Huitle et al., "Electrochemical Alternatives for Drinking Water Disinfection," Chem Int Ed Engl. 47(11), pp. 1998-2005 (2008).
Erickson et al., "Inactivation of Protozoan Parasites in Food, Water, and Environmental Systems," J Food Prot. 69(11), pp. 2786-808 (Nov. 2006).
Kerwick et al., "A Methodology for the Evaluation of Disinfection Technologies," J Water Health. 3(4), pp. 393-404 (Dec. 2005).
Feng et al., "Water Disinfection by Electrochemical Treatment," Bioresour Technol. 94(1), pp. 21-5 (Aug. 2004).
Avchinnikov, "Sanitary Assessment of Currently Available Methods of Drinking Water Disinfection (Review)," Gig Sanit. (2), pp. 11-20 (Mar.—Apr. 2001). (English abstract provided).
Okochi et al., "Electrochemical Disinfection of Drinking Water Using an Activated-Carbon-Fiber Reactor Capable of Monitoring its Microbial Fouling," Appl Microbiol Biotechnol. 47(1):18-22 (Jan. 1997).
Feedlyte, http://www.distrilyte.com/index.php?p.=4 (Nov. 6, 2007).
Envyrolyte, http://www.envirolyte.com/group.shtml (Mar. 17, 2009).
Envirocleanse, LLC, http://www..eco-enviro.com (Nov. 20, 2008).
Health Homes Plus, http://www.healthyhomesplus.com/articles/anolyte_water.htm (Jan. 19, 2010).
Lenfant, Biomedicine and pharmacology 58 (2004), p 248-54.
International Search Report in PCT/US2011/44947 (Feb. 29, 2012).
Supplementary EP Search Report in EP11810437 (Dec. 12, 2013).
D. Frumkin et al.: "Authentication of forensic DNA samples", Forensic Sci. Int. Genet. Sep. 20, 2001, XP26829808.
D. Frumkin et al.: "DNA-methylation-based forensic tissue identification", Forensic Sci. Int. Genet. vol. 5, No. 5, Dec. 6, 2010, pp. 517-524, XP028275689.
Hambidge A. "Reviewing Efficacy of Alternative Water Treatment Techniques-Part 2"; Health Estate. Aug. 2001; 55 (7):24-6.

* cited by examiner

COMPOSITIONS AND METHODS FOR THE PREVENTION AND TREATMENT OF CARDIOVASCULAR DISEASES

This application claims priority to U.S. Provisional Application Ser. No. 61/129,883, filed on Jul. 25, 2008.

BACKGROUND OF THE INVENTION

Cardiovascular diseases, which include coronary heart disease (heart attacks), cerebrovascular disease, raised blood pressure (hypertension), peripheral artery disease, rheumatic heart disease, congenital heart disease and heart failure, derive from dysfunctional conditions of the heart, arteries, and veins that supply oxygen to vital life-sustaining organs, including the brain and the heart itself. Major causes of cardiovascular disease are tobacco use, physical inactivity and an unhealthy diet.

Heart attacks and strokes are mainly caused by a blockage in the inner walls of the blood vessels that prevents blood from flowing to the heart or the brain. Arteriosclerosis and atherosclerosis are excess buildup of fat or plaque deposits, respectively, that cause narrowing of the veins that supply oxygenated blood to the heart and may lead to ischemic heart disease, an obstruction of blood flow to the heart. Excess fat or plaque buildup may also cause high blood pressure (hypertension), a disease known as "The Silent Killer" because the first warning sign is an angina attack, a deadly heart attack or a stroke. Kidney disorders, obesity, diabetes, smoking, excess alcohol, stress, and thyroid and adrenal gland problems can also exacerbate a high blood pressure condition.

Damage to the heart tissues from cardiovascular diseases or heart surgery disrupts the natural electrical impulses of the heart and results in cardiac arrhythmia. Sudden fluctuations in heart rate can cause cardiac irregularities and insufficiencies, including palpitations, supraventricular tachycardia, fibrillation faintness or dizziness, and even initiate a heart attack.

Mismatch of cardiac output during strenuous exercise may lead to muscle damage, induce fatigue and affect athletic performance.

Arteries spasm and irregular contraction and expansion of blood vessels in the brain may reduce flow of blood from the occipital lobe and trigger migraines.

Levels of total blood cholesterol above 250 mg/dL, LDL cholesterol above 130 mg/dL (3.0 mmol/L), HDL cholesterol below 35 mg/dL and lipoprotein(a) level greater than 30 mg/dL may also lead to a heart attack or stroke.

Infections of the heart, known as carditis and endocarditis, may occur as a result of a weak immune system, liver problems, heart surgery, or from an autoimmune disorder like rheumatic fever.

Heavy smoking may cause Buerger's disease, also known as thrombophlebitis obliterans, an acute inflammation and thrombosis (clotting) of arteries and veins of the hands and feet, which is often associated with intense pain in the extremities, claudication in the feet and/or hands, numbness and/or tingling in the limbs, skin ulcerations, gangrene and Raynaud's phenomenon, a condition in which the distal extremities turn white upon exposure to cold.

Peripheral arterial occlusive disease may cause diabetic ulcers, which are the most common foot injuries leading to lower extremity amputation in diabetic patients.

Often, there are no symptoms of underlying cardiovascular diseases and a heart attack or stroke may be the first warning. Early medical detection and treatment is available, however, is not always effective. Angiograms, bypass surgery and angioplasty are invasive and traumatic procedures associated with high cost and often requiring additional therapy and/or intervention.

Accordingly, there is a need in the art for improved prevention and treatment options for cardiovascular diseases and the present invention satisfies this need.

SUMMARY OF THE INVENTION

It is therefore an object of the invention to provide solutions to the aforementioned deficiencies in the art.

It is an object of the present invention to provide a therapeutic composition for the prevention and treatment of dysfunctional cardiovascular conditions.

It is a further object of the invention to provide a method for treating or preventing a dysfunctional cardiovascular condition in a subject in need thereof.

To accomplish these and other objectives, the invention provides a therapeutic composition comprising an electro-activated solution with a negative oxidation-reduction potential (ORP) in a range between −50 mV and −500 mV, a conductivity between 11 and 15 mS/cm and a pH in the range between 6.5 and 7.6.

The composition of the invention, which is prepared by mixing two electro-activated solutions, Solution A with a stable negative oxidation-reduction potential, and Solution B with a stable positive oxidation-reduction potential, prior to use, is stable for at least 48 hours when stored at 4°-8° C.

Further, the invention provides a stable therapeutic composition comprising an electro-activated solution, which has a stable positive oxidation-reduction potential (ORP) in the range between +500 mV and +900 mV for a period of at least 12 months when stored at 15°-25° C. in no direct sunlight, and a pH in the range between 6.5 and 7.8.

Moreover, the invention provides a stable therapeutic composition comprising an electro-activated solution, wherein the electro-activated solution has an oxidation-reduction potential (ORP) in the range between −500 mV and −900 mV for a period of at least 12 months when stored at 15°-25° C. in no direct sunlight, and a pH in the range between 3.2 and 4.5.

In a preferred aspect of the invention, the electro-activated solutions of the invention comprise magnetic dipole stabilized water (MDSW). In one aspect of the invention, the electro-activated solutions further comprises an organic molecule of organic molecule of the formula

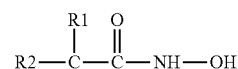

wherein R1 is NH$_2$ and R2 is

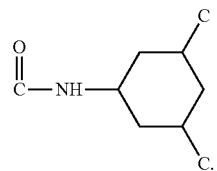

In another aspect of the invention, the organic molecule has a longer carbon chain.

In a specific embodiment, the electro-activated solution comprises 0.5-10% magnesium sulfate hexahydrate, 5.0-20.0% ascorbic acid, 0.2-2.0% niacinamide, 0.2-2% pyridoxin HCl, 0.01-2.0% calcium D pantothenate, 0.1-1.0% thiamin HCl, 0.01-0.1% riboflavin, 0.001-0.1% cyanocobalamin, 0.05-10% sodium lactate and 5-500 ml magnetic dipole stabilized water.

In another specific embodiment, the electro-activated solution comprises 190-220 mg nicotinic acid, 9.5-11.0 mg thiamin HCl, 1.9-2.2 mg riboflavin, 285-330.0 mg folic acid, 23.7-27.5 μg cyanocobalimin, 23.7-27.5 μg pyridoxin HCl, 100% magnetic dipole stabilized water, 1.04-1.2 g magnesium chloride, 1.9-2.2% 2-di-ethyl amino ethanol, 228-264.0 mg ascorbic acid and 0.4-0.75% amino acetic acid. In a further aspect of the invention, the electro-activated solution (MDSW) contains inorganic salts at an ionic concentration of 50 to 500 parts per million. In a preferred aspect of the invention, the inorganic salts are sodium chloride, sodium bicarbonate and magnesium sulfate, and the electro-activated solution contains 0.5-1.0 g/l of sodium bicarbonate, 8.0-10.0 g/l of sodium chloride and 4.5-7.5 g/l of magnesium sulfate.

In an additional embodiment, the invention provides a method for treating or preventing a dysfunctional cardiovascular condition in a subject in need thereof, comprising administering to the subject a therapeutic composition comprising a therapeutically effective amount of electro-activated solution. The electro-activated solution has a negative oxidation-reduction potential (ORP) in a range between −50 mV and −500 mV, a conductivity between 11 and 15 mS/cm and a pH in the range between 6.5 and 7.6. In a preferred aspect of the invention, the electro-activated solution comprises magnetic dipole stabilized water (MDSW). In one aspect of the invention, the electro-activated solution further comprises an organic molecule of the formula

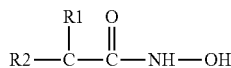

wherein R1 is NH$_2$ and R2 is

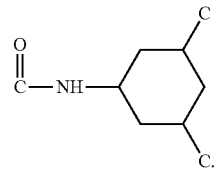

In another aspect of the invention, the organic molecule has a longer carbon chain.

In a specific embodiment, the electro-activated solution comprises 0.5-10% magnesium sulfate hexahydrate, 5.0-20.0% ascorbic acid, 0.2-2.0% niacinamide, 0.2-2% pyridoxin HCl, 0.01-2.0% calcium D pantothenate, 0.1-1.0% thiamin HCl, 0.01-0.1% riboflavin, 0.001-0.1% cyanocobalamin, 0.05-10% sodium lactate and 5-500 ml magnetic dipole stabilized water. In another specific embodiment, the electro-activated solution comprises 190-220 mg nicotinic acid, 9.5-11.0 mg thiamin HCl, 1.9-2.2 mg riboflavin, 285-330.0 mg folic acid, 23.7-27.5 μg cyanocobalimin, 23.7-27.5 μg pyridoxin HCl, 100% magnetic dipole stabilized water, 1.04-1.2 g magnesium chloride, 1.9-2.2% 2-di-ethyl amino ethanol, 228-264.0 mg ascorbic acid and 0.4-0.75% amino acetic acid. In a further aspect of the invention, the electro-activated solution (MDSW) contains inorganic salts at an ionic concentration of 50 to 500 parts per million. In a preferred aspect of the invention, the inorganic salts are sodium chloride, sodium bicarbonate and magnesium sulfate, and the electro-activated solution contains 0.5-1.0 g/l of sodium bicarbonate, 8.0-10.0 g/l of sodium chloride and 4.5-7.5 g/l of magnesium sulfate.

In one aspect of the invention, the composition is administered to the subject to be treated by parenteral injection. In preferred embodiments of the invention, the composition is diluted in isotonic intravenous (IV) fluid and administered intra-arterially, intravenously or intra-arterially and intravenously. Following treatment, the composition may be administered periodically as a maintenance therapy. The subject to be treated may have or may be at risk of having a dysfunctional cardiovascular condition. Dysfunctional cardiovascular conditions include, but are not limited to, coronary heart disease, cerebrovascular disease, hypertension, peripheral artery disease, rheumatic heart disease, congenital heart disease, heart failure, cardiac insufficiency, palpitations, supraventricular tachycardia, fibrillation, faintness, dizziness, fatigue, migraine, high levels of total blood cholesterol and/or high LDL cholesterol, low level of HDL cholesterol, high level of lipoprotein, carditis and endocarditis, diabetic ulcer, thrombophlebitis, Raynauds disease, claudication and gangrene.

DETAILED DESCRIPTION OF THE INVENTION

The compositions and methods of the present invention are for the prevention and treatment of dysfunctional cardiovascular conditions. The aim of the invention is to provide effective, non-invasive methods to prevent and treat a dysfunctional cardiovascular condition in a subject in need thereof, by restoring cellular integrity and trans membrane potential, modulating cellular membrane permeability and enhancing the transfer of molecules and ions through the cell membranes.

The terms "subject" and "patient" are used interchangeably, and are meant to refer to any mammal, including humans, that has, or is at risk of developing, a dysfunctional cardiovascular condition. The subject or patient is typically human, however, other suitable subjects or patients include, but are not limited to, laboratory animals, such as mouse, rat, rabbit, or guinea pig, farm animals and domestic animals or pets. Non-human primates are also included.

As used herein, a "therapeutically effective amount" is an amount effective to elicit a cellular response that is clinically significant.

As used herein, by "dysfunctional cardiovascular conditions" it is meant to include cardiac and vasculatory malfunctions, such as coronary heart disease, cerebrovascular disease, hypertension, peripheral artery disease, rheumatic heart disease, congenital heart disease, heart failure, cardiac insufficiency, palpitations, supraventricular tachycardia, fibrillation, faintness, dizziness, fatigue, migraine, high levels of total blood cholesterol and/or LDL cholesterol, low level of HDL cholesterol, high level of lipoprotein, infections of the heart such as carditis and endocarditis, diabetic ulcer, thrombophlebitis, Raynauds disease, claudication and gangrene.

As used herein, "nicotinic acid", "niacinamide" and "folic acid" may be used interchangeably in the solutions and compositions of the invention.

As used herein, magnesium salts, including magnesium sulfate and magnesium chloride, may be used interchangeably in the solutions and compositions of the invention.

Free oxygen radicals, also known as reactive oxygen species (ROS), cause much damage to macromolecules, including lipids, proteins and nucleic acids. One major toxic effect of oxygen radicals is damage to cellular membranes, including the plasma, mitochondrial and endo-membrane systems, which is initiated by lipid peroxidation and is accompanied by increased membrane rigidity, decreased activity of membrane-bound enzymes, altered activity of membrane receptors and altered membrane permeability. Furthermore, oxygen radicals can also directly attack membrane proteins and induce lipid-lipid, lipid-protein and protein-protein crosslinking, which in turn affects membrane function.

Because of their reactivity, free oxygen radicals may react with DNA, resulting in mutations that can adversely affect the cell cycle and potentially lead to cancer and malignancies. Moreover, oxygen free radicals are involved in cardiovascular diseases, the aging process, neurodegenerative diseases, including ALS, Parkinson's disease and Alzheimer's disease, cataractogenesis, atherosclerosis, diabetes mellitus, ischemia-reperfusion injury, kwashiorkor, senile- and drug-induced deafness, schizophrenia, atherosclerosis and alcohol-induced liver damage.

There is strong evidence in the literature that free oxygen radicals oxidize low density lipoprotein (LDL), which is then engulfed by phagocytes to form foam cells and plaques in the cardiovascular wall. These plaques harden and narrow the blood vessels and impair blood flow, thus depriving the heart of oxygen and nutrients. In addition, ischemia is often followed by reperfusion injury, which is caused by inadequate supplies of intracellular antioxidants. Ischemia and reperfusion are a major cause of strokes.

There is also increasing evidence that mismatch of cardiac output during strenuous exercise causes release of free oxygen radicals, which contribute to muscle damage and induce fatigue and/or injury.

Moreover, it has been reported that the activity of the anti-oxidant enzymes superoxide dismutase (SOD), catalase (CAT) and glutathione peroxidase (GSH-Px) is significantly lower in subjects suffering from migraine. SOD is known to protect against vasoconstriction or vasospasm induced by superoxide radicals. Migraine is a potential risk factor or marker for atherosclerosis-related diseases.

Cardiovascular Disease

At any given time, the distribution of blood in a person's body will be approximately:

64% veins
13% arteries
9% pulmonary vessels
7% heart
7% arterioles and capillaries.

Although the heart weighs less than 1% of the total body weight, it relentlessly receives nearly 5% of the total blood flow (which may explain why the arteries of the heart can so easily develop problems). Congenital defects and infectious disease can strike anywhere, but by far the most common disease occurs in the arteries: atherosclerosis.

Blockages can occur in veins as well as in arteries, but those in the veins tend to be caused by blood clots, or thrombi, rather than by atherosclerosis. Thrombophlebitis (or often called phlebitis) most commonly involves clotting of blood and inflammation of a vein in the leg. This can be serious if a portion of the clot becomes detached, travels through the heart and gets pumped to the lung where it blocks a pulmonary artery as a pulmonary embolism. About 10% of people with pulmonary embolism die within an hour.

Clotting of blood in the veins can occur when blood flow is slow or stagnant. This can occur during long periods of immobilization such as when a person is confined to a hospital bed, cramped in a crowded airplane on a long flight or driving for an extended period.

Atherosclerosis

Atherosclerosis (hardening of the arteries) occurs "naturally" with aging as a result of cross-linking of macromolecules like proteins and polysaccharides. Atherosclerosis refers to the formation and hardening of fatty plaques (atheromas) of the inner surface of the arteries. In atherosclerosis, the arteries not only harden, they narrow, sometimes narrowing so much that hardly any blood can get through. Such narrows vessels are easily blocked by constriction or objects in the bloodstream.

The internal surface of an artery is covered with a single layer of endothelial cells that are pressed against each other like flagstones on a terrace. Atherosclerosis begins with injury to endothelial cells, exposing portions of the artery surface below the endothelium. Free radicals, chemicals in cigarette smoke or other irritants could be responsible for the injury, as could turbulence and mechanical force due to high blood pressure. Platelets (round cells half as large as red blood cells) clump around the injured endothelial cells and release prostaglandins, which cause the endothelial cells to proliferate like cancer. LDL-cholesterol particles release their fat into the areas made porous by prostaglandins. Macrophages (scavenger white blood cells) engorge themselves on oxidized LDL-cholesterol until they become unrecognizable "foam cells" that invade atheromas. Then the atheromas are hardened by fibrin (which forms scar tissue) and finally by calcium patches. A vicious circle often arises with scar tissue attracting more platelets and LDL-engorged macrophages.

Atherosclerotic Cardiovascular Disease

Atherosclerosis can occur in any artery. Most commonly it occurs in the aorta, the artery that receives blood directly from the heart. Since the aorta is the largest artery in the body, it is rarely critically narrowed by atheromas. Nonetheless, atherosclerosis can contribute to aneurysms (ballooning of an artery, responsible for only one-fortieth of the mortality rate of heart attack—an aortic aneurysm killed Albert Einstein, who refused to be operated upon.) The most frequent life-threatening problems, however, are caused by the arteries supplying the heart, the brain and the kidneys, in that order.

Cholesterol

Since the blood is 80% water, fats will not dissolve in the blood. Therefore, fats need to be attached to carrier molecules to travel through the bloodstream. The principle carrier molecules for fat are albumin, chylomicrons, Very Low Density Lipoprotein (VLDL), Low Density Lipoprotein (LDL) and High Density Lipoprotein (HDL). Free Fatty Acids (FFAs) are attached to albumin, whereas triglycerides are mainly transported by chylomicrons and VLDL. Cholesterol and phospholipid are primarily transported by LDL and HDL.

Cholesterol is supplied to cells primarily by the attachment of LDL to specific LDL receptors on cell membranes. Thyroid hormone lowers blood cholesterol by increasing the number of LDL receptors on cells. For most people, atherosclerosis due to excessive LDL-cholesterol in the blood is the result of a high level of dietary saturated fat resulting in high LDL-cholesterol production by the liver.

The primary function of HDL seems to be to remove excess cholesterol from the bloodstream. LDL can directly release cholesterol into arterial areas made porous by prostaglandins—whereas HDL can scoop up this loose cholesterol and return it to the liver. Thus, HDL deficiency can be as serious an atherosclerosis risk as LDL-cholesterol excess. A 1% reduction in blood cholesterol is generally associated with a 2% reduction in risk of coronary artery disease, within "normal" levels of blood cholesterol.

Free Fatty Acids

Free fatty acids are a major source of energy for many organs, including the heart. Triglycerides are hydrolyzed into FFAs and glycerol by the enzyme lipase, which is found both inside cells and on the surface of the endothelial cells of capillaries. Phospholipid is an essential constituent of cell membranes. Cholesterol is also an essential constituent of cell membranes, particularly in the nervous system. Cholesterol is also the principle precursor of cortisone and sex hormones. 93% of cholesterol is found in cells and only 7% in plasma.

Compositions

The compositions of the present invention are useful for the prevention and treatment of dysfunctional cardiovascular conditions in subjects in need thereof, and contain electro-activated solutions of inorganic salts and anti-oxidants with a stable negative oxidation-reduction potential (ORP) in a range between −50 mV and −500 mV, a conductivity between 11 and 15 mS/cm and a pH in the range between 6.5 and 7.6.

The stable compositions of the invention are prepared by mixing two electro-activated solutions, Solution A with a stable negative oxidation-reduction potential, and Solution B with a stable positive oxidation-reduction potential, immediately prior to use.

The electro-activated solutions with a stable positive or negative oxidation-reduction potential may be obtained by exposing an aqueous salt solution to electric current. The electric current electro-activates the molecules, atoms and ions in the solution and the ions are redistributed in the electric field. As a result, the aqueous solution in the cathode chamber (catholyte) is charged with a negative ORP and acquires bio-regenerative properties. The aqueous solution in the anode chamber (anolyte) is charged with a positive ORP and acquires antiseptic properties.

The electro-activated solutions with a stable positive or negative oxidation-reduction potential may be prepared by any method known in the art. Preferably, sterile, purified water is electro-activated using an open plate palladium-coated electrode in a ceramic-type housing of a module containing ferrous and non-ferrous alloys capable of imparting a fixed magnetic field of at least 7.5 Gauss over a period of time of at least 1.75 minutes at a flow rate of at least 0.75 liter/minute. The electro-activated water thus obtained, which has an initial positive oxidation-reduction potential (ORP) in a range between +700 mV and +900 mV, is then collected in a sterilized, air-free and endotoxin-free vessel and used to prepare Solution A and Solution B. Both solutions are used as a diluent for vitamins, salts and minerals.

Solution A is prepared by adding 2-diethylaminoaceto xylidide to the vessel filled with the electro-activated water until complete dissolution; adding ascorbic acid or sodium ascorbate, which are both strong anti-oxidants, in a concentration of 83.6-95.5 g/L and 90.0-100.0 g/L, respectively, to reach a stable, negative ORP in a range between −500 mV and −900 mV and stirring until dissolved; adding salts, vitamin and minerals and lastly cyanocobalamin to reach a pH between 3.2 and 4.5; and bubbling nitrogen through the mixture.

In a specific embodiment, 1.0 liter of Solution A contains the following vitamins, salts and minerals:

| Ascorbic acid | 83.6-95.5 g/L |
| Magnesium Sulphate hexahydrate | 57.1-64-7 g/L |
| 2-diethylaminoaceto,xylidide | 28.5-32.3 g/L |
| Niacinamide | 9.4-10.6 g/L |
| Pyridoxin HCL | 9.4-10.6 g/L |
| Riboflavin-5-phosphate sodium | 0.18-029 g/L |

-continued

| Thiamin HCL | 5.7-6.5 g/L |
| Cyanocobalamin crystalline | 0.17-0.2 g/L |
| Electrochemically activated water + | 997.50 ml |

To prepare Solution B, sodium bicarbonate, sodium chloride, a salt selected from magnesium sulfate and magnesium chloride and optionally calcium are added to the vessel filled with the electro-activated water until complete dissolution. The solutes increase ionization and produce a stably charged anti-inflammatory solution. A stabilizer may be also added to the solution in an amount of 0.5% mass/volume to increase conductive ionization and produce a stably charged solution with a stable, positive oxidation-reduction potential in a range between +500 mV and +900 mV and a pH between 6.5 and 7.8. The stabilizer may be mixed into the solution by agitation or a sonicator bath and the solution is immediately sealed to prevent entry of oxygen.

In a specific embodiment, 1.0 liter of Solution B contains the following salts and minerals:

| Sodium Bicarbonate USP | 82.4-93.2 g/L |
| Magnesium Sulphate hexahydrate | 19.1-21.8 g/L |
| Electrochemically activated water + | 998.5 ml |

Both solutions A and B are stable for a period of at least 12 months when stored at 15°-25° C. in no direct sunlight.

Solution A and Solution B are then mixed prior to administration to produce a composition with a stable negative oxidation-reduction potential (ORP) in a range between −50 mV and −500 mV, a conductivity between 11 and 15 mS/cm and a pH in the range between 6.5 and 7.6. In a preferred embodiment, the stable composition comprises 0.5-10% magnesium sulfate hexahydrate, 5.0-20.0% ascorbic acid, 0.2-2.0% niacinamide, 0.2-2% pyridoxine HCl, 0.01-2.0% calcium D pantothenate, 0.1-1.0% thiamin HCl, 0.01-0.1% riboflavin, 0.001-0.1% cyanocobalamin, 0.05-10% sodium lactate and 5-500 ml magnetic dipole stabilized water. The composition thus produced is stable for at least 48 hours when stored at 4°-8° C., and may be administered as is or diluted in isotonic intravenous (IV) fluid.

The present inventors unexpectedly discovered that the electro-activated solutions of the invention have high anti-oxidant properties. In particular, the inventors unexpectedly found that parenteral administration of the electro-activated solutions to a subject with or at risk of developing a dysfunctional cardiovascular condition prevents or eliminates the cardiovascular condition. Without being bound to any theory, it is believed that the solutions of the invention improve oxygen delivery to the arteries, veins and cardiac muscle and the transport of anti-oxidants and minerals to the bloodstream by causing changes in the concentration gradient of the cellular membranes which in turn modulate transport of physiological ions, such as sodium and potassium. In addition, it is believed that the electro-activated solution of the invention improves membrane permeability and thus increases the rate of transport of the minerals and anti-oxidants in the solution. Furthermore, parenteral injection of the composition into the bloodstream provides for the fast and prompt reaching of high levels of nutrients, anti-oxidants and minerals in the blood, thus eliminating the need for digestive enzymes and providing an antidote to conditions caused by cardiovascular dysfunctions.

The compositions of the invention are added to isotonic intravenous (IV) fluid and parenterally administered to the subject by intravenous injection, intra-arterial injection, or by intravenous and intra-arterial injection. Following treatment, the composition may be administered periodically as a maintenance therapy. Typically, when administered by intravenous injection, the composition is administered in an amount of 50-300 ml daily, biweekly, weekly, bimonthly or monthly for a period from 14 days to six months, and when administered by intra-arterial injection, the composition is administered in an amount of 10-50 ml daily, biweekly, weekly, bimonthly or monthly for a period from 14 days to six months.

The treatment envisioned by the invention can be used for subjects with a pre-existing condition, or for subjects predisposed to a cardiovascular disease or dysfunction.

EXAMPLES

Example 1

Preparation of the Electro-Activated Solution

An electro-activated aqueous solution is prepared using an open plate palladium-coated electrode in a ceramic-type housing of a module containing ferrous and non-ferrous alloys capable of imparting a fixed magnetic field of at least 7.5 Gauss over a period of time of at least 1.75 minutes at a flow rate of at least 0.75 liter/minute. The electro-activated water thus obtained, which has an initial positive oxidation-reduction potential (ORP) in a range between +700 mV and +900 mV, is then collected in a sterilized, air-free and endotoxin-free vessel and used as a diluent for vitamins, salts and minerals. The electro-activated water thus obtained, which has an initial positive oxidation-reduction potential (ORP) in a range between +700 mV and +900 mV, is then collected in a sterilized, air-free and endotoxin-free vessel and used to prepare Solution A and Solution B. Both solutions are used as a diluent for vitamins, salts and minerals.

Solution A is prepared by adding 2-diethylaminoaceto xylidide to the vessel filled with the electro-activated water until complete dissolution; adding ascorbic acid or sodium ascorbate, which are both strong anti-oxidants, in a concentration of 83.6-95.5 g/L and 90.0-100.0 g/L, respectively, to reach a stable, negative ORP in a range between −500 mV and −900 mV and stirring until dissolved; adding salts, vitamin and minerals and lastly cyanocobalamin to reach a pH between 3.2- and 4.5; and bubbling nitrogen through the mixture.

In a specific embodiment, 1.0 liter of Solution A contains the following vitamins, salts and minerals:

| | |
|---|---|
| Ascorbic acid | 83.6-95.5 g/L |
| Magnesium Sulphate hexahydrate | 57.1-64-7 g/L |
| 2-diethylaminoaceto,xylidide | 28.5-32.3 g/L |
| Niacinamide | 9.4-10.6 g/L |
| Pyridoxin HCL | 9.4-10.6 g/L |
| Riboflavin-5-phosphate sodium | 0.18-029 g/L |
| Thiamin HCL | 5.7-6.5 g/L |
| Cyanocobalamin crystalline | 0.17-0.2 g/L |
| Electrochemically activated water + | 997.50 ml |

To prepare Solution B, sodium bicarbonate, sodium chloride, a salt selected from magnesium sulfate and magnesium chloride and optionally calcium are added to the vessel filled with the electro-activated water until complete dissolution. The solutes increase ionization and produce a stably charged anti-inflammatory solution. A stabilizer may be also added to the solution in an amount of 0.5% mass/volume to increase conductive ionization and produce a stably charged solution with a stable, positive oxidation-reduction potential in a range between +500 mV and +900 mV and a pH between 6.5 and 7.8. The stabilizer may be mixed into the solution by agitation or a sonicator bath and the solution is immediately sealed to prevent entry of oxygen.

In a specific embodiment, 1.0 liter of Solution B contains the following salts and minerals:

| | |
|---|---|
| Sodium Bicarbonate USP | 82.4-93.2 g/L |
| Magnesium Sulphate hexahydrate | 19.1-21.8 g/L |
| Electrochemically activated water + | 998.5 ml |

Both solutions A and B are stable for a period of at least 12 months when stored at 15°-25° C. in no direct sunlight.

Solution A and Solution B are then mixed prior to administration to produce a composition with a stable negative oxidation-reduction potential (ORP) in a range between −50 mV and −500 mV, a stable pH between 6.5 and 7.6, and a conductivity in the range between 11 and 15 mS/cm.

The final mixture thus obtained comprises the following ingredients:

| | |
|---|---|
| Magnesium sulfate hexahydrate | 0.5-10% |
| Sodium Bicarbonate | 0.5-10% |
| Ascorbic Acid | 5.0-20% |
| Niacinamide | 0.2-2.0% |
| Pyridoxin HCl | 0.005-0.2% |
| Calcium D Pantothenate | 0.01-2.0% |
| Thiamin HCl | 0.1-1.0% |
| Riboflavin | 0.01-0.1% |
| Cyanocobalamin | 0.001-0.1% |
| Magnetic Dipole Stabilized Water | 5.0-500 ml |
| 2-di-ethylaminoethanol | 1.0-3.0% |

Example 2

The Coronary Calcium Scan

The coronary calcium scan is a test that assists in showing whether a patient is at risk of developing a coronary artery disease (CAD), by determining the presence of plaque (fatty deposits) in blood vessels. The presence and amount of calcium detected in a coronary artery indicates the presence and amount of atherosclerotic plaque. Since calcium deposits appear years before the development of heart disease symptoms such as chest pain and shortness of breath, a coronary calcium scan is most useful for people who are at moderate risk of having a heart attack within the next 10 years, and may help doctors decide whether a patient needs treatment. The calcified plaque burden caused by calcium deposits is measured with the Calcium Score, also called the Agatston Calcium Score, which is computed for each of the coronary arteries based upon the volume and density of the calcium deposits. The calcified plaque burden does not correspond directly to the percentage of narrowing in the artery but does correlate with the severity of the underlying coronary atherosclerosis. The score is then used to determine the calcium percentile, which compares the calcified plaque burden in a subject to the calcified plaque burden in other asymptomatic men and women of the same age. The calcium score, in combination with the percentile, enables the physician to determine the risk of developing symptomatic coronary artery disease and to measure the progression of disease and the effectiveness of treatment.

A score of zero indicates the absence of calcified plaque burden and significant coronary artery narrowing, although it does not entirely rule out the presence of soft, non-calcified plaque or the possibility of a cardiac event. A subject with a score of zero has a very low likelihood of a cardiac event over at least the next 3 years. A score greater than zero indicates at least some coronary artery disease. As the score increases, so does the likelihood of a significant coronary narrowing and coronary event over the next 3 years, compared to people with lower scores. Similarly, the likelihood of a coronary event increases with increasing calcium percentiles. Table 1 below shows the relation between the calcium score and the risk of coronary artery disease.

TABLE 1

| Calcium Score | Implication | Risk of Coronary Artery Disease |
| --- | --- | --- |
| 0 | No identifiable plaque | Very low, generally less than 5% |
| 1-10 | Minimal identifiable plaque | Very unlikely, less than 10% |
| 11-100 | Definite, at least mild atherosclerotic plaque | Mild or minimal coronary narrowings likely |
| 101-400 | Definite, at least moderate atherosclerotic plaque | Mild coronary artery disease highly likely, significant narrowings possible |
| 401 or higher | Extensive atherosclerotic plaque | High likelihood of at least one significant coronary narrowing |

Example 3

The Calcium Plaque Burden of a Subject with a High Calcium Score

The plaque burden of a 45 years old male with a family history of hypertension and diabetes mellitus type 2 and an Agatston calcium score of 467 was determined. The calcium score was 17 in the left main coronary artery, 20 in the right coronary artery, 264 in the left anterior descending coronary artery, 166 in the circumflex artery and 0 in the posterior descending artery. The high calcium score indicates that the subject has a very high risk of coronary artery disease. The plaque burden data are shown in Table 2 below.

TABLE 2

Calcium Plaque Burden of a patient with a score of 467

| Region | Volume (mm3) | Calcium Score (Agatston) |
| --- | --- | --- |
| Left Main | 26 | 17 |
| Right Coronary Artery | 38 | 20 |
| Left Anterior Descending | 251 | 264 |
| Circumflex | 145 | 166 |
| Posterior Descending Artery | 0 | 0 |
| Other 1 | 0 | 0 |
| Other 2 | 0 | 0 |
| Other 3 | 0 | 0 |
| Total | 460 | 467 |

Example 4

Treatment of Subjects with the Electro-Activated Solution

Twenty male and female individuals between the ages of 24 and 63 were randomly selected for the treatment, based on age, physical activity and body mass index (BMI). Subjects with a family history of cardiovascular diseases, diabetes mellitus or cancer were included in the treatment. The individuals were subjected to a complete physical examination, blood and urine analyses, calcium score measurement and radiological examination. The calcium score was 0 in nine subjects; 1 in one subject; 24 in two subjects; 32 in one subject; 40 in one subject; 42 in one subject; 46 in one subject; 57 in one subject; 155 in one subject; 482 in one subject; and 1668 in one subject. The radiological study performed on the twenty individuals showed that individuals with a calcium score of 0 had no calcified plaques, whereas subjects with a calcium score between 24 and 57 had calcified plaques in the left anterior descending artery (LAD) and were at mild risk for coronary artery diseases. Subjects with a calcium score of 155 or 482 showed calcification in the right coronary artery (RCA) and left anterior descending artery (LAD) with a definite risk for coronary artery disease. The patient with a calcium score of 1668 showed calcification of the right coronary artery, left main artery, left anterior descending artery (LAD), the diagonal and circumflex arteries, confirming a very high risk for coronary artery diseases.

All subjects had their blood pressure and pulse taken before and after each treatment session and treated with an electro-activated solution prepared as in Example 1. The solution was administered to each subject by intravenous injection in an amount of 100 ml of sterile diluent (0.9% sodium chloride injection) for 35 to 55 minutes once or twice a week for a period ranging from two weeks to two months.

At the end of the treatment, all subjects reported feeling extremely well and energetic, improvement in sleeping patterns and mental alertness and a decrease in anxiety and stress level. Several subjects reported an improvement in visual, hearing and sensory acuity and an increase in hair growth. A few subjects reported increased libido and decrease in weight. Some subjects reported the beneficial sensation of hot flushes and tingling in the extremities. One subject reported an improvement in pre-menstrual symptoms. One obese subject whose ankles were dark blue because of the excessive weight, reported that the ankles had turned pink after the fourth treatment. The smokers in the group reported a decrease in nicotine intake at the end of treatment. A subject suffering from angina attacks before treatment reported a decrease in chest pains after beginning of treatment. No side effects were reported.

Example 5

The Effect of the Treatment on the Calcium Score

The calcium score was measured in the individuals subjected to the treatment with the electro-activated solution at the end of treatment. Table 3 below shows the calcium score of nine individuals with an initial medium to high calcium score before and after 12 treatment sessions. The data in Table 3 clearly show a positive effect of the treatment on individuals with an initial calcium score of 46 and above.

TABLE 3

| Patient | Calcium Score Before Treatment | Calcium Score After 12 Treatment Sessions | Percentage of Increase or Decrease |
| --- | --- | --- | --- |
| 1 | 24 | 25 | 4% Increase |
| 2 | 24 | 26 | 8% Increase |
| 3 | 32 | 31 | 3% Decrease |
| 4 | 40 | 42 | 5% Increase |

TABLE 3-continued

| Patient | Calcium Score Before Treatment | Calcium Score After 12 Treatment Sessions | Percentage of Increase or Decrease |
|---|---|---|---|
| 5 | 46 | 29 | 37% Decrease |
| 6 | 57 | 40 | 29% Decrease |
| 7 | 155 | 121 | 22% Decrease |
| 8 | 482 | 441 | 9% Decrease |
| 9 | 1668 | 1539 | 8% Decrease |

Example 6

Treatment of Patients with Angina

Patients A and B are diagnosed with stable angina. Patient A is treated with conventional medications, including heparin, aspirin and beta blocker. Patient B is administered the electro-activated solution prepared as in Example 1 by intravenous injection in an amount of 200 ml/day for 30 days.

After one month of treatment both patients are examined. Patient A, after a brief period of remission, shows symptoms of angina. Patient B, treated according to the method of the invention, shows complete remission and symptoms of angina have not reappeared after one year.

Example 7

Treatment of Patients with Buerger's Disease

The effect of the method of treatment according to the invention is studied on subjects with Buerger's Disease. 18 heavy-smoker males between the ages of 20 and 40 and 5 women over the age of 50 are diagnosed with Buerger's Disease. Symptoms include intense pain in the extremities (claudication), numbness and/or tingling in the limbs, skin ulcerations and gangrene. 8 subjects show signs of Raynaud's disease, a phenomenon in which the distal extremities turn white upon exposure to cold. Angiograms of all patients demonstrate lack of blood flow to the vessels of the hand. An electro-activated solution prepared as in Example 1 is administered to each subject by intravenous injection in an amount of 200 ml/day for 20 days. Within 15 days from the beginning of treatment, the symptoms of Buerger's Disease disappear and angiograms show net improvement in blood flow.

The invention claimed is:

1. A therapeutic composition for parenteral injection comprising an electro-activated solution, wherein the electro-activated solution has an oxidation-reduction potential (ORP) in the range between −50 mV and −500 mV for a period of at least 12 months, a conductivity in the range between 11 and 15 mS/cm and a pH in the range between 6.5 and 7.6; and wherein the electro-activated solution consists essentially of:

| | |
|---|---|
| Nicotinic Acid | 190-220 mg; |
| Thiamin | 9.5-11.0 mg; |
| Riboflavin | 1.9-2.2 mg; |
| Folic Acid | 285.0-330.0 mg; |
| Cyanocobalamin | 23.7-27.5 µg; |
| Pyridoxin | 23.7-27.5 µg; |
| Electro-Activated Water | to 10 ml; |
| Magnesium sulfate hexahydrate and | 50-1000 mg; |
| Ascorbic Acid | 228-264.0 mg. |

2. The therapeutic composition of claim 1, wherein the electro-activated solution further comprises 0.5-1.0 g/l of sodium bicarbonate and 8.0-10.0 g/l of sodium chloride.

* * * * *